(12) United States Patent
Krebs et al.

(10) Patent No.: US 7,784,975 B2
(45) Date of Patent: Aug. 31, 2010

(54) APPARATUS FOR LINEAR ILLUMINATION OF A MOVING PRODUCT WEB

(75) Inventors: Stephan Krebs, Landsberg (DE); Alfred Eder, Altenmuenster (DE); Juergen Eisen, Augsburg (DE); Lars Zwerger, Augsburg (DE)

(73) Assignee: Texmag GmbH Vertriebsgesellschaft, Thalwil (CH)

( * ) Notice: Subject to any disclaimer, the term of this patent is extended or adjusted under 35 U.S.C. 154(b) by 308 days.

(21) Appl. No.: 12/217,183

(22) Filed: Jul. 2, 2008

(65) Prior Publication Data
US 2009/0010006 A1 Jan. 8, 2009

(30) Foreign Application Priority Data
Jul. 4, 2007 (EP) .................. 07013083

(51) Int. Cl.
*F21V 7/00* (2006.01)
(52) U.S. Cl. .............. 362/296.01; 362/217.05; 362/253; 362/296.05; 362/341; 362/609; 250/227.11; 250/227.31; 250/548; 250/559.19; 235/454
(58) Field of Classification Search .................. 362/217.01–217.02, 217.05–217.09, 253, 362/257, 296.01, 296.05–296.08, 341, 347, 362/602, 608–609, 611–614; 250/227.11, 250/227.26, 227.31, 548, 559.19, 559.26; 235/454, 456
See application file for complete search history.

(56) References Cited

U.S. PATENT DOCUMENTS

| 4,002,919 A | 1/1977 | Linard |
| 4,041,321 A * | 8/1977 | Linard ............... 250/559.15 |
| 5,166,532 A | 11/1992 | Brunner et al. |

FOREIGN PATENT DOCUMENTS

| DE | 3928159 A1 | 2/1991 |
| EP | 1154225 | 11/2001 |

* cited by examiner

*Primary Examiner*—Sandra L O'Shea
*Assistant Examiner*—Meghan K Dunwiddie
(74) *Attorney, Agent, or Firm*—Robert L. Epstein; Epstein Drangel Bazerman & James, LLP

(57) ABSTRACT

An apparatus (1) serves for linear illumination of a moving product web (6), the apparatus (1) having at least one light source (4) emitting light. In order to achieve high luminance in a linear subregion of the product web (6), at least a portion of the light emitted by the light source (4) is reflected towards the product web (6) by at least one tubular reflector (5). The tubular reflector (5) in this case has at least one light exit slit (7) which is assigned to the product web (6). Moreover, the tubular reflector has at least one observation slit (8) which lies opposite the light exit slit (7). The illuminated product web (6) can be observed through this observation slit (8) by means of a line camera (2).

Figure 1:
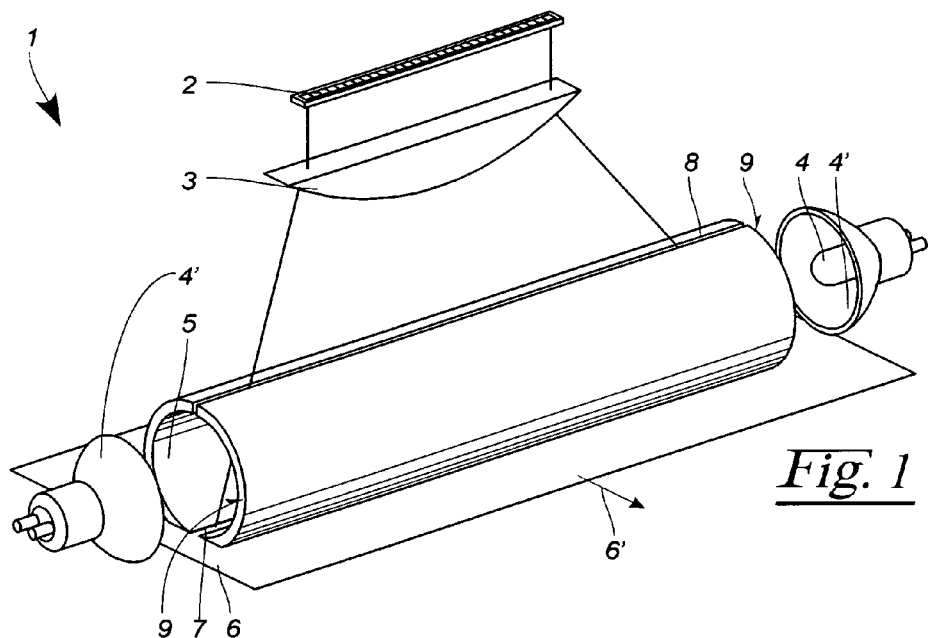

13 Claims, 3 Drawing Sheets

APPARATUS FOR LINEAR ILLUMINATION OF A MOVING PRODUCT WEB

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON COMPACT DISC

Not Applicable

BACKGROUND OF THE INVENTION

1. Field of the Invention

The invention relates to an apparatus for linear illumination of a moving product web.

2. Description of Prior Art Including Information Disclosed Under 37 CFR 1.97 and 1.98

EP-B-1 154 225 discloses an illumination apparatus for a moving product web which enables optimum scanning of the product web with the aid of a camera. This has both a directional and a diffuse light source in order to be able to scan the most varied product webs. This illumination apparatus has proved itself in practice and forms the point of departure of the present invention.

DE-A-39 28 159 A1 discloses a generic edge sensor which has a light source and a photodetector. Both the light source and the photodetector are surrounded by reflector screens which are in each case open towards the product web. This arrangement is adequate for the application of the transmitted light method. In the reflection method, in the case of which light source and receiver are arranged on the same side of the product web, it is, however, mandatory to illuminate the product web at an acute angle, since otherwise the light reflected by the product web could fail to be detected.

BRIEF SUMMERY OF THE INVENTION

The invention is based on the object of providing an apparatus of the type mentioned at the beginning which attains a high luminance in conjunction with diffuse light.

This object is achieved according to the invention, by means of the following features.

The apparatus in accordance with the invention serves the purpose of linear illumination of a moving product web. It has at least one light-emitting light source, it being of no importance how the light source generates the light. For example, the light source could be a halogen lamp, a light-emitting diode, a neon tube, an incandescent lamp or a laser. This enumeration is not, however, to be understood as exhaustive. Particularly in the case of the use of modern line cameras of high pixel density for optimum scanning of the product web, very small photodiodes are used which require a very large luminance in order to attain a photosignal which can be effectively evaluated. If a line camera is used, linear illumination of the product web is sufficient in principle, since the camera can in any case evaluate only a linear region of the product web. It is advantageous in this case to illuminate the product web in as linear a fashion as possible with a small line width in order to implement the highest possible luminance on the small evaluated surface. This would be possible in principle with directed light which is focused onto the product web via appropriate optics. However, this measure has the disadvantage that it is impossible for a multiplicity of product webs that require diffuse light to be scanned adequately. Diffuse light is essential as regards printed image detection, in particular. In order to bring diffuse light with high luminance onto a linear evaluation region of the product web, it is provided according to the invention that the light emitted by the light source is reflected towards the product web by at least one tubular reflector. The light is preferably multiply reflected in the tubular reflector until it reaches a light exit slit facing the product web. This light exit slit is illuminated in this case with high luminance and can therefore also be optically scanned effectively by highly resolving cameras with a small pixel structure. For this purpose, the tubular reflector has at least one observation slit at which light reflected by the product web can exit. This observation slit lies opposite the light exit slit. A line camera can therefore be provided above the observation slit so that it looks onto the illuminated product web through the observation slit. The observation slit can in this case remain narrow so that only a little light from the light source leaves the observation slit directly. Nevertheless, the product web can be scanned in a planar fashion when it moves transverse to the observation slit. In this way, a very low light intensity of the at least one light source suffices to generate a high luminance in the region of the light exit slit. Consequently, the illumination apparatus not only becomes energy efficient, but also reduces problems with the dissipation of heat from the light source. In order to adjust the camera above the observation slit, it is sufficient to find that point at which the observed image brightness is at a maximum. Consequently, the correct adjustment of the camera in relation to the observation slit of the illumination apparatus can be attained very easily.

If the light exit slit or the observation slit is to be of variable design, it is advantageous if the respective slit penetrates the tubular reflector completely. If both slits penetrate the tubular reflector, it consists of two parts which can be adjusted with respect to one another in any way desired, this being possible by means of suitable manipulators. If, by contrast, only one of the slits completely penetrates the reflector, this slit can be adjusted in width by simply deforming the reflector. The deformation is preferably performed elastically.

Alternatively, it is advantageous when the light exit or observation slit is bridged by at least one web. This web is preferably located in at least one end region of the tubular reflector. The camera can therefore be set in such a way that it does not scan the web region. The webs therefore do not in any way impede the optical detection of the product web. The webs themselves increase the stability of the tubular reflector, however, and so the latter is easier to handle.

Particularly in the case of the use of only one light source at the end face of the tubular reflector, or in the case of illumination of the reflector in a fashion distributed over its length, it is advantageous when the reflector is closed in a reflecting fashion at at least one end. This reflecting termination prevents exiting of the light at the ends of the tubular reflector and therefore increases the luminance at the light exit slit.

In order, in particular, not to impair the detection of the product web by a camera, it is advantageous when the at least one light source is provided at at least one end of the reflector. The light source itself therefore lies outside the detection region of the camera and can, moreover, be changed without any problem. Alternatively, or in addition, there is also the idea of coupling the light source into the end of the reflector such that a larger structural margin remains for mounting the light source. Particularly in the case of heat sensitive product webs such as, for example, plastic webs, it is more advantageous for the light source to be arranged at a greater distance from the product web.

Glass or plastic fibres as well as mirrors have proved themselves for coupling in the light source. These permit the light output by the light source to be effectively coupled into the tubular reflector.

In order to attain a high illumination intensity of the product web, it is important that the product web is guided as closely as possible past the light exit slit of the tubular reflector. In order to facilitate this arrangement, it is favourable when the reflector is flattened on the product web side. The product web can therefore be guided nearer up to the light exit slit of the reflector by approximately the material thickness of the reflector.

In principle, the reflector could reflect the incident light diffusely. However, it is advantageous when the reflector is designed in a specularly reflecting fashion. In this way, it is possible to attain relatively high reflectivities in principle such that the decrease in luminance with the number of reflections remains lower at the reflector. Moreover, the specularly reflecting surfaces are less sensitive to soiling than the diffusely reflecting surfaces. There is also the idea of using optically coated reflectors in order further to increase the reflectivity.

Finally, it is advantageous when the reflector is designed with a cross section which is substantially circular or elliptical. This shape ensures a high luminance in the light exit slit.

Further advantages and features of the present invention are presented in the following detailed description with reference to the accompanying figure which contains an exemplary embodiment of the present invention. It should be understood, however, that the drawing serves merely for the purpose of illustrating the invention and does not restrict the scope of protection of the invention.

BRIEF DESCRIPTION OF THE SEVERAL VIEWS OF DRAWINGS

Figure 2:
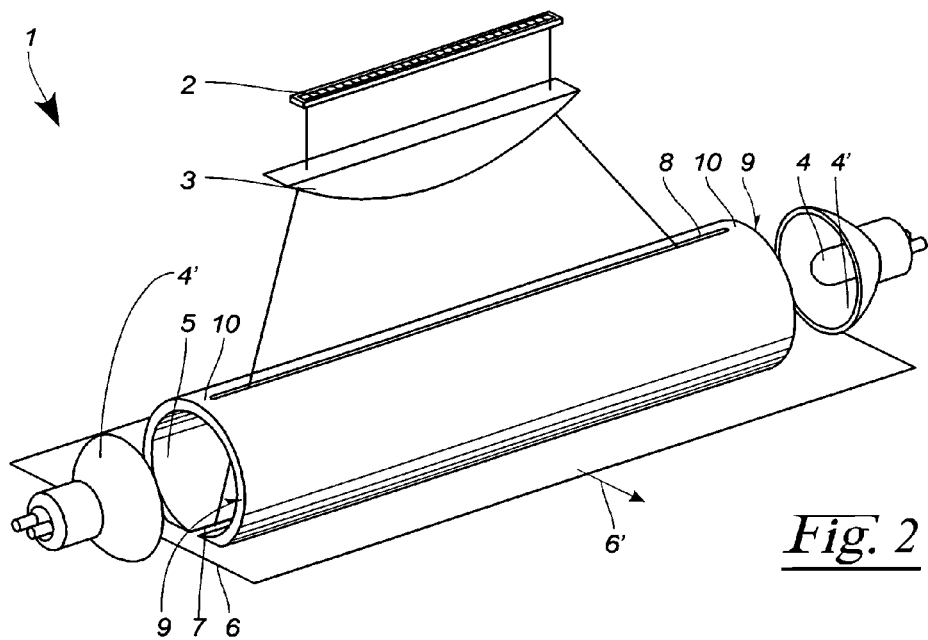
Figure 3:
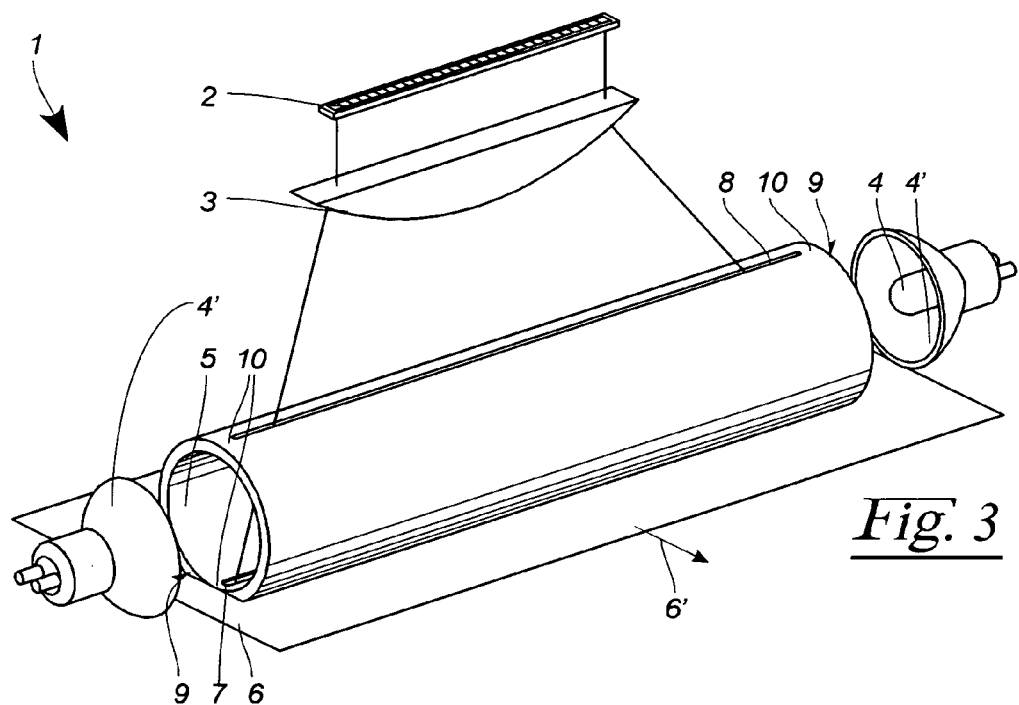
Figure 4:
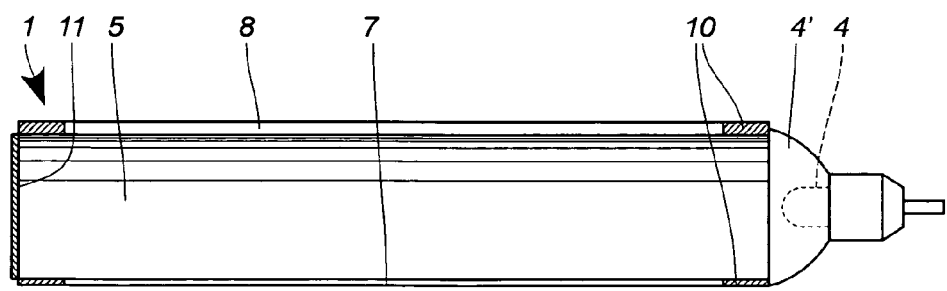
Figure 5:
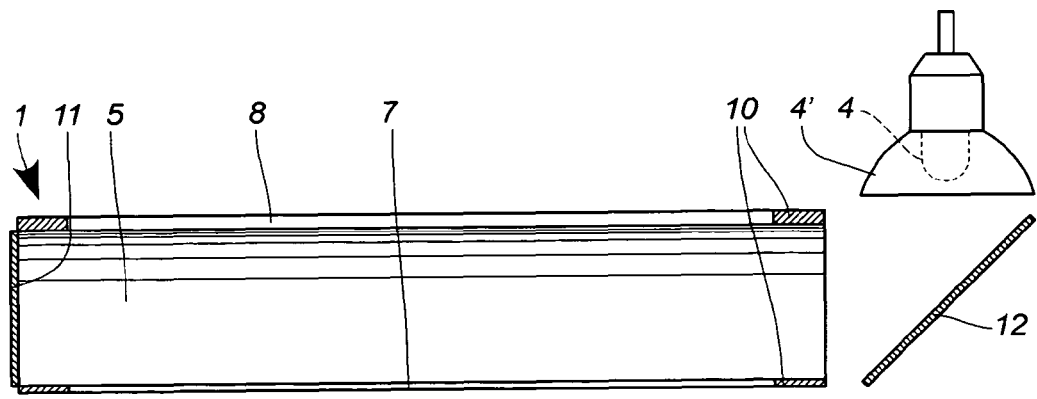
Figure 6:
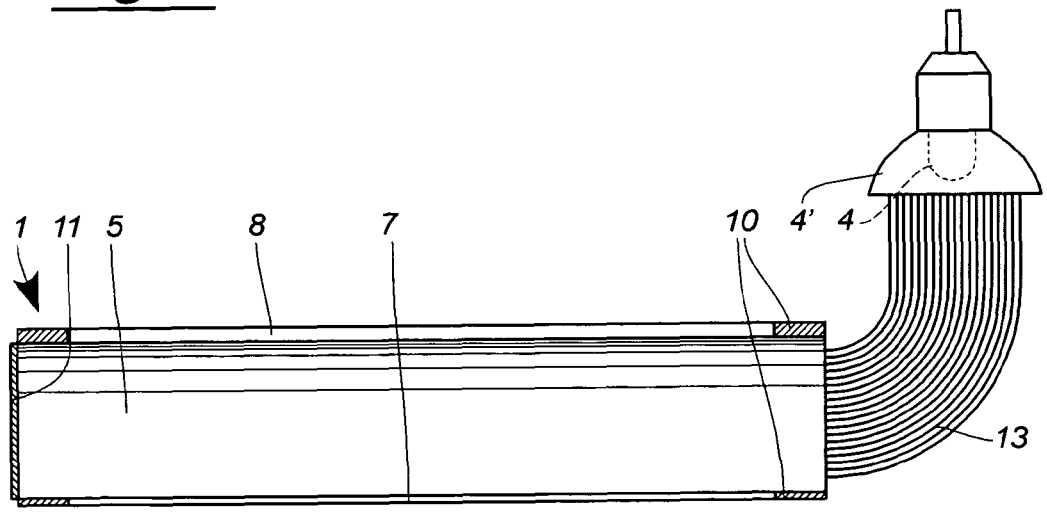
Figure 7:
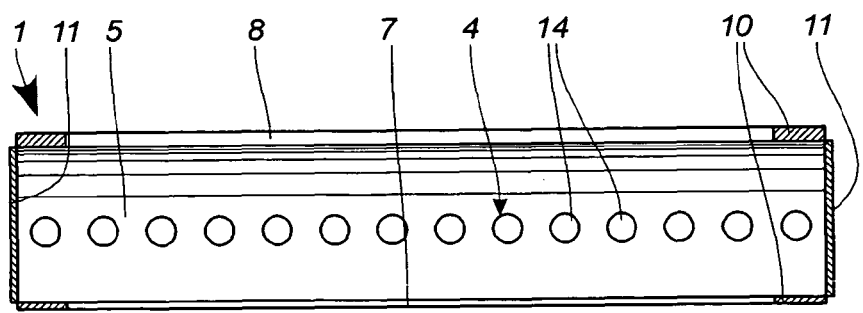

To these and to such other objects that may hereinafter appears, the present invention relates to a heating apparatus as described in detail in the following specification and recited in the annexed claims, taken together with the accompanying drawing in which shows:

FIG. 1: a diagrammatic, three-dimensional illustration of a first embodiment of an illumination apparatus, FIG. 2: a diagrammatic, three-dimensional illustration of a second embodiment of an illumination apparatus, FIG. 3: a diagrammatic, three-dimensional illustration of a third embodiment of an illumination apparatus, FIG. 4: a diagrammatic sectional illustration of a fourth embodiment, FIG. 5: a diagrammatic sectional illustration of a fifth embodiment, FIG. 6: a diagrammatic sectional illustration of a sixth embodiment, and FIG. 7: a diagrammatic sectional illustration of a seventh embodiment.

DETAILED DESCRIPTION OF THE INVENTION

FIG. 1 shows a three-dimensional, diagrammatic exploded illustration of an illumination apparatus 1 which is assigned a line camera 2. The line camera 2 has an objective 3 in the form of a cylindrical lens which focuses the recorded image onto the line camera 2.

The illumination apparatus 1 has two light sources 4 which are provided at both end faces 9 of a tubular reflector 5. Provided around the two light sources 4 are reflectors 4' which close the two end faces of the reflector 5.

On its side facing a product web 6 moving in the direction 6', the tubular reflector 5 has a light exit slit 7 which completely penetrates the reflector 5. In the region of the light exit slit 7, the reflector 5 is flattened on the product web side in order to be able to guide the product web 6 more closely up to the reflector 5. Provided opposite the light exit slit 7 is an observation slit 8 which likewise completely penetrates the reflector 5. The two slits 7, 8 therefore divide the reflector 5 into two separate parts which must be held appropriately relative to one another and relative to the product web 6.

The line camera 2 and the objective 3 are adjusted relative to the reflector 5 in such a way that these are aligned exactly with the observation slit 8, and the line camera 2 sees the product web 6 in the light exit slit 7 through the reflector 5. A high luminance in the region of the light exit slit 7 results from multiple reflections of the light of the two light sources 4 inside the reflector 5. Both the light exit slit 7 and the observation slit 8 can be varied in width by adjusting the two reflector halves with aspect to one another.

FIG. 2 shows an alternative embodiment of the illumination apparatus 1 in accordance with FIG. 1, only the differences relating to the embodiment in accordance with FIG. 1 being examined below. In all the embodiments, identical reference numerals are used to name identical parts.

In the case of the embodiment in accordance with FIG. 2, the observation slit 8 no longer completely penetrates the reflector 5 and so a web 10 remains in each case at both ends 9. These webs 10 ensure an improved mechanical stability of the reflector 5, it no longer being possible to adjust the width of the observation slit 8—as occasioned by the webs 10. However, the width of the light exit slit 7 can be varied by electrical deformation of the reflector 5.

As an alternative to the embodiment in accordance with FIG. 2, the webs 10 can also be provided in the region of the light exit slit 7 such that the light exit slit 7 is of fixed width. In this case, the observation slit 8 can have its width varied by deforming the reflector 5.

FIG. 3 shows a further alternative embodiment in the case of which both the light exit slit 7 and the observation slit 8 no longer completely penetrate the reflector 5. At both ends 9, webs 10 bridge both the light exit slit 7 and the observation slit 8.

The result of this measure is that the entire reflector 5 is mechanically stable and thus easy to handle. The widths of the light exit slit 7 and of the observation slit are, however, prescribed in this case and can no longer be varied.

FIG. 4 shows a diagrammatic sectional illustration through a further embodiment of the illumination apparatus. This illumination apparatus 1 corresponds substantially to the embodiment in accordance with FIG. 3, only one light source 4 being provided. Provided at the end 9 opposite the light source 4 is a reflecting, axial termination 11 of the reflector 5 whose purpose is to prevent light from exiting at this site. The termination 11 can be designed to reflect both diffusely and specularly.

This measure can also be implemented with the reflector 5 in accordance with FIG. 1 or 2. FIG. 5 shows a further embodiment of the illumination apparatus 1 in accordance with FIG. 4. In this embodiment, the light source 4 is coupled into the reflector 5 via a deflecting mirror 12. In this way, the distance of the light source 4 from the product web 6 can be increased, and this is of particular importance in the case of heat sensitive product webs 6.

This arrangement of the light source 4 can also be implemented with the reflector 5 in accordance with FIG. 1 or 2.

FIG. 6 shows a further alternative embodiment, in the case of which the light source 4 is coupled into the reflector 5 via fibre bundles 13. These fibre bundles 13 permit an even larger distance of the light source 4 from the product web 6, thermal radiation additionally being suppressed. Consequently, the reflector 5 remains cold and no longer stresses the product web 6 thermally.

This embodiment of the illumination can also be implemented with the aid of the reflector 5 in accordance with FIG. 1 or 2.

Finally, FIG. 7 shows a further diagrammatic sectional illustration of an illumination apparatus 1. In the case of this apparatus, the light source 4 is implemented by light-emitting diodes 14 which are preferably designed as white light LEDs. Alternatively, it is also possible to use other LEDs. Use is made, in particular, of infrared LEDs in the form of GaAs LEDs. This depends chiefly on the aim of the examinations to be carried out. Thus, white light is to be preferred when analyzing print patterns, while infrared light is chiefly to be preferred for analyzing weave patterns as well as the fundamental thread structure.

Since the light-emitting diodes 14 are located inside the reflector 5, the latter is terminated at both ends by mirrors 11.

This illumination apparatus 1 can also be implemented with the aid of the reflector 5 in accordance with FIG. 1 or 2.

Since some exemplary embodiments of the present invention are not shown or described, it must be understood that a multiplicity of changes and modifications of this exemplary embodiment described are possible, without departing from the essential idea and scope of protection of the invention defined by the claims.

LIST OF REFERENCE NUMERALS

1 Illumination apparatus
2 Line camera
3 Objective
4 Light source
4' Reflector
5 Reflector
6 Product web
6' Movement direction
7 Light exit slit
8 Observation slit
9 End
10 Web
11 Termination
12 Deflecting mirror
13 Fibre bundles
14 Light-emitting diode

The invention claimed is:

1. Apparatus for linear illumination of a moving product web, at least partially reflecting light, the apparatus comprising at least one tubular reflector and at least one light source emitting light, at least a portion of said light emitted by said light source being reflected by said reflector towards said product web said reflector having a region facing the product web, said region being provided with at least one light exit slit said reflector being provided with at least one observation slit for the exit of said light being reflected by the product web, said at least one observation slit being opposite to said light exit slit.

2. Apparatus according to claim 1, wherein said light exit slit completely penetrates the tubular reflector.

3. Apparatus according to claim 2, wherein said observation slit completely penetrates said tubular reflector.

4. Apparatus according to claim 1 wherein said reflector having end regions, and said light exit slit is bridged by at least one web in at least one of said end regions.

5. Apparatus according to claim 1 wherein said reflector having end regions, and said observation slit is bridged by at least one web in at least one of said end regions.

6. Apparatus according to claim 1, wherein said reflector having end regions, and said reflector is closed in a reflecting fashion at least one of said end regions.

7. Apparatus according to claim 1, wherein said reflector having end regions and said at least one light source being provided at least one of said end regions of the reflector.

8. Apparatus according to claim 1, wherein said reflector having end regions and said at least one light source being coupled to least one of said end regions of the reflector.

9. Apparatus according to claim 8, wherein said at least one light source is coupled into said reflector via at least one of glass fibres, plastic fibres and deflecting mirrors.

10. Apparatus according claim 1, wherein said reflector is flattened around said light exit slit.

11. Apparatus according claim 1, wherein said reflector having an inside and being specularly reflective on said inside.

12. Apparatus according to claim 1, wherein said reflector having a cross section and said cross section being substantially circular.

13. Apparatus according to claim 1, wherein said the reflector having a cross section and said cross section being substantially ellipical.

* * * * *